May 14, 1974 O. J. KLAAS Plant Pat. 3,550
APPLE TREE
Filed Jan. 8, 1973
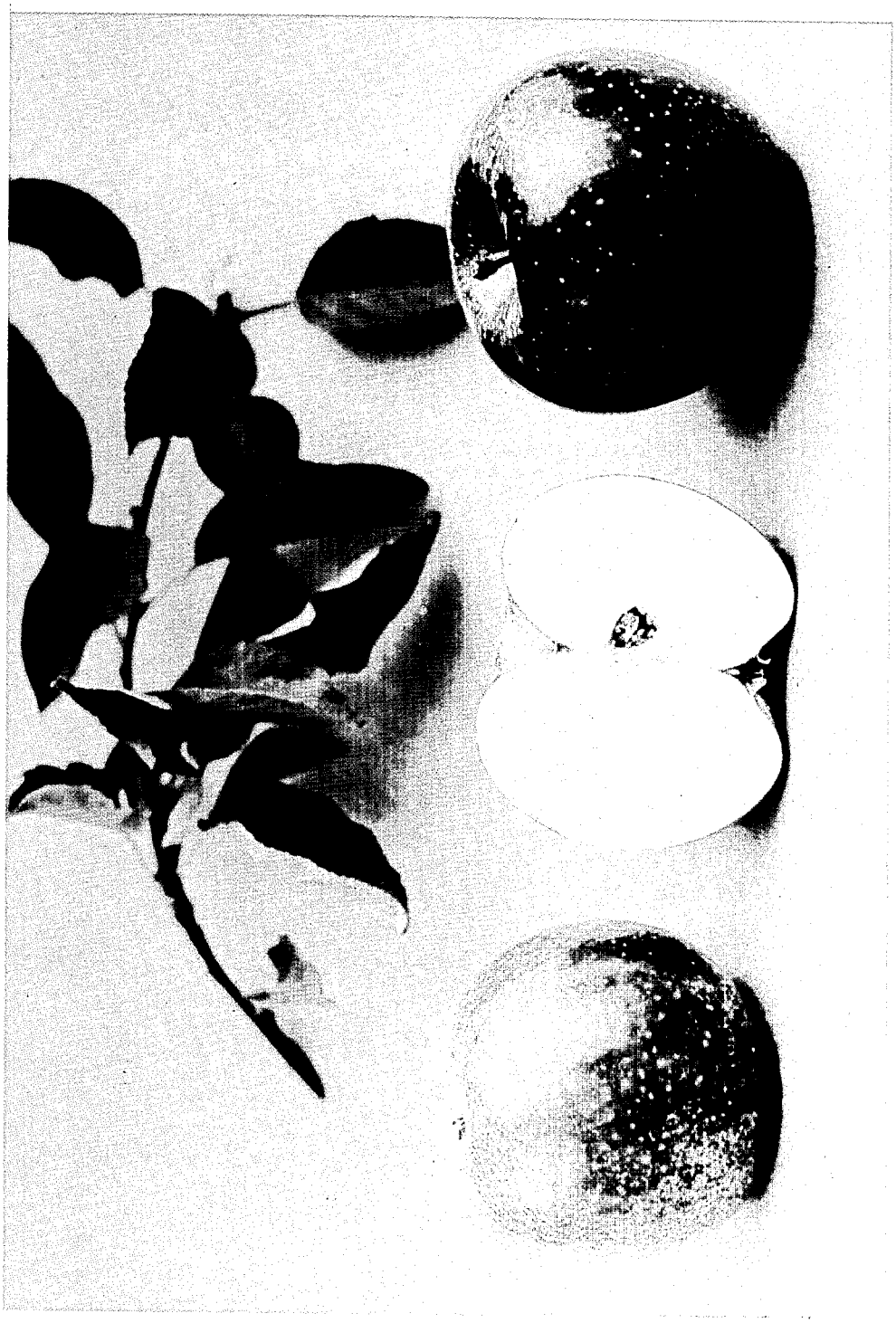

United States Patent Office

Plant Pat. 3,550
Patented May 14, 1974

3,550
APPLE TREE

Otto J. Klaas, Batchtown, Ill., assignor to Stark Bro's Nurseries & Orchards Company, Louisiana, Mo.

Filed Jan. 8, 1973, Ser. No. 321,915
Int. Cl. A01h *5/03*
U.S. Cl. Plt.—34 1 Claim

The present invention relates to a new and distinct variety of apple tree which was discovered by me as a sprout from the root of a tree of the well-known "Delicious" apple variety which has been widely distributed in the trade by the assignee hereof under the registered trademark "Starking," said discovery having been made by me in my cultivated orchard located at Batchtown, Illinois.

In the expectation that the new sprout referred to above would prove to be a new sport of the "Starking Delicious" apple variety, I carefully preserved the same and allowed it to grow and bear fruit. I also reproduced the same asexually by grafting as performed by me in my orchard aforementioned in Calhoun County, Illinois. My continuous and prolonged observations of the original sprouted tree and its progeny have convinced me that it is a new apple variety which is distinguished from its parent, as well as from all other apple varieties of which I am aware, as evidenced by the following unique combination of principal characteristics which are particularly outstanding therein:

(1) A late blooming and fruit-ripening habit comparable to "Rome Beauty" (unpatented);
(2) A fruit and cavity shape comparable to that of "Rome Beauty," with a burrowed basin resembling that of the fruit of "Starking Delicious";
(3) Thick and waxy fruit skin having a deep red color resembling the skin of "Starking Delicious," with the texture of the fruit being firmer and the fruit flavor being more acid than the fruit of "Starking Delicious" and more pleasing than the fruit flavor of "Rome Beauty"; and
(4) An ability of the fruit to hang on the tree until fully colored and ripe without premature dropping.

The accompanying drawing shows typical specimens of the foliage and fruit of my new apple variety, with one of the fruit specimens being shown in cross-section, and all as depicted in color.

The following is a detailed description of the new variety, with color terminology in accordance with Ridgway's Color Standards and Nomenclature (hereinafter abbreviated as (R)), Munsell Color Chart (hereinafter abbreviated as (M)), and the Horticulture Colour Guide (hereinafter abbreviated as (HCG)), except where general color terms of ordinary dictionary significance are obvious:

Locality where grown and observed: Calhoun County, Illinois.

Dates of first and last pickings: About October 6 and October 20, respectively.

Tree: Medium large size; vigorous; upright-spreading; tall; round-topped; rapid growing; hardy; very productive; regular bearing.

*Trunk.*—Medium stockiness; medium smoothness.

*Branches.*—Medium thickness; smooth; much-branched. Color (current season shoots)—Vandyke Red, Plate XIII, color No. I', tone m (R).

Lenticels—Few; small.

*Leaves.*—Medium small; wide; medium short; oval; taper-pointed; medium thickness; rugose. Length—About 3 inches. Width—About 1⅝ inches. Color—Moderate Olive Green. Hue 7.5 GY 4/4 (M). Margin—Finely serrate. Petiole—Medium length (about 1 inch); medium slender.

Flowers: Medium late; medium large.

*Dates of first and full bloom.*—About April 25 and May 2, respectively.

*Color.*—White, with pink areas at margin and on lower side of petals corresponding to Carmine, Plate 21/2, page 21, Vol. 1 (HCG).

Fruit:

*Maturity when described.*—Eating ripe.

*Size.*—Uniform. Axial diameter—About 2⅞ inches. Transverse diameter—About 3 inches.

*Form.*—Globose at both base and apex.

*Cavity.*—Symmetrical; flaring; even. Depth—About ⅝ inch. Breadth—About 1¼ inches. Markings—None.

*Basin.*—Symmetrical; rounded at base; wide base. Depth—About 5/16 inch. Breadth—About 1 inch. Markings—None.

*Stem.*—Medium slender; pubescent. Length—About ⅞ inch. Breadth—About 3/32 inch. Markings—None.

*Calyx.*—From open to closed; persistent; broadly lanceolate; acute; about 3/16 inch long; separated; reflexed from base at apex; both outer and inner surfaces pubescent.

*Skin.*—Thick; tough; glossy; waxed. Dots—Conspicuous, many, large, raised, ruptured, circular; color of dots—Pale Orange Yellow, Hue 7.5 YR 9/4 (M); distribution—all over. Ground color—Brilliant Greenish Yellow, Hue 7.5 Y 9/8 (M). Color markings—Blushed, self-colored, dull; color—Chrysanthemum Crimson, Plate 824/2, page 169, Vol. 2 (HCG). Bloom—Moderate. Scarf-skin—Light, color—Gray. General color effect—Over-all deep red; bright when polished.

*Flesh*—Juicy. Color—Dull yellowish white. Texture—Firm; fine; crisp. Flavor—Subacid. Aroma—Distinct. Quality—Good.

*Core.*—Distant. Bundle area—Medium small; oblate; symmetrical; acute at base. Halves of area—Unequal. Bundles—Inconspicuous, in one whorl; color—Green tinged. Alternate bundle—Reaches tube at stamens. Core lines—Clasping. Cross section—Distinct. Carpellary area—Indistinct; small. Calyx tube—Glabrous toward base and apex, cone-shaped; entire depth—about ¼ inch. Styles—Present; fleshy at base; distinct toward base; pubescent throughout. Stamens—In one distinct whorl; marginal. Auxiliary cavity—Wanting. Seed cells—Axile, closed; cell walls—approximate, thin, tough; length—about ⅞ inch; breadth—about ½ inch. Longitudinal section—Broadly oval; obtuse at apex. Surface—Fissured; tufted. Cross section—Narrow.

Seeds: From 8 to 10 and usually all perfect; no more than 2 per cell.

*Length.*—About ¼ inch.

*Breadth.*—About 3/16 inch.

*Form.*—Obtuse.

*Color.*—Liver Brown, Plate XIV, color No. 7′, tone M (R).

Use: Market; dessert; culinary.

Keeping quality: Good, about 120 days in ordinary storage.

Disease resistance: Good resistance to usual apple diseases, and particularly to bacterial blight, as determined by comparison with other apple varieties grown under the same conditions in Calhoun County, Illinois.

I claim:

1. A new and distinct variety of apple tree, substantially as herein shown and described, characterized particularly as to novelty by the unique combination of a late blooming and fruit-ripening habit comparable to "Rome Beauty" (unpatented), a fruit and cavity shape comparable to that of "Rome Beauty," with a burrowed basin resembling that of the fruit of "Starking Delicious," thick and waxy fruit skin having a deep red color resembling the fruit skin of "Starking Delicious," with the texture of the fruit being firmer and the fruit flavor being more acid than the fruit of "Starking Delicious" and more pleasing than the fruit flavor of "Rome Beauty," and an ability of the fruit to hang on the tree until fully colored and ripe without premature dropping.

No references cited.

ROBERT E. BAGWILL, Primary Examiner